(12) United States Patent
Moors

(10) Patent No.: US 8,562,813 B2
(45) Date of Patent: Oct. 22, 2013

(54) SYSTEM AND METHOD FOR PERFORMING A POLARIZATION SCAN IN SITU

(75) Inventor: Thomas Michael Moors, Greenville, SC (US)

(73) Assignee: General Electric Company, Schenectady, NY (US)

( * ) Notice: Subject to any disclaimer, the term of this patent is extended or adjusted under 35 U.S.C. 154(b) by 344 days.

(21) Appl. No.: 13/012,108

(22) Filed: Jan. 24, 2011

(65) Prior Publication Data

US 2012/0186995 A1     Jul. 26, 2012

(51) Int. Cl.
*G01N 27/48*     (2006.01)
*G01N 17/02*     (2006.01)
*G01N 27/416*     (2006.01)

(52) U.S. Cl.
USPC ........................................ 205/775.5; 204/404

(58) Field of Classification Search
USPC ............ 204/404, 286; 205/775.5; 73/86, 768; 422/53
See application file for complete search history.

(56) References Cited

U.S. PATENT DOCUMENTS

| | | | |
|---|---|---|---|
| 4,155,814 A * | 5/1979 | Tejfalussy et al. | ............ 205/776 |
| 4,425,193 A | 1/1984 | Taylor | |
| 4,861,453 A * | 8/1989 | Matsuoka et al. | ............ 204/404 |
| 5,945,594 A | 8/1999 | Kendig et al. | |
| 6,369,589 B1 | 4/2002 | Gao et al. | |
| 6,740,216 B2 | 5/2004 | Diakonov et al. | |
| 6,792,796 B2 | 9/2004 | Hammonds | |
| 6,902,661 B2 * | 6/2005 | Thomas et al. | ............ 205/776.5 |
| 7,325,392 B2 | 2/2008 | Stancovski et al. | |
| 7,519,481 B2 | 4/2009 | Perrin et al. | |

* cited by examiner

*Primary Examiner* — Alex Noguerola
(74) *Attorney, Agent, or Firm* — Dority & Manning, PA

(57) ABSTRACT

A system for performing an in-situ polarization scan of a component surface includes a sensor connected to the component surface at a sensor connection, and the sensor generates a signal reflective of a current flow at the sensor connection. A power supply connected to the component surface at an electrical connection produces a voltage potential at the electrical connection. An electrolyte coats the sensor connection and the electrical connection. A method for performing an in-situ polarization scan of a component surface includes sensing a current flow on the component surface, generating a voltage potential on the component surface, and placing an electrolyte over at least a portion of the component surface.

19 Claims, 2 Drawing Sheets

… … …

SYSTEM AND METHOD FOR PERFORMING A POLARIZATION SCAN IN SITU

FIELD OF THE INVENTION

The present invention generally involves a system and method for performing a polarization scan in-situ. Particular embodiments of the present invention may be used to predict corrosion rates and maintenance and repair needs based on the in-situ polarization scan.

BACKGROUND OF THE INVENTION

Machinery and equipment operated in harsh environments are often subject to accelerated corrosion rates which, if not monitored or controlled, can result in premature aging and eventually failure of the machinery and equipment. Stainless steel alloys have been developed to reduce or inhibit general corrosion and/or the onset of localized corrosion such as crevice and/or pitting corrosion. Components made from the steel alloys may be inspected for corrosive damage and repaired or replaced as necessary based on observed or extrapolated corrosive damage.

Electrochemical polarization scans may also be performed on components made from steel alloys to identify the components' resistance to corrosion. For example, FIG. 1 provides an exemplary polarization plot or curve that correlates the corrosion potential ($E_{corr}$) across the surface of a passivated steel alloy component to the onset of particular forms of corrosion. As shown in FIG. 1, the passive oxide film may protect the surface of the steel alloy component by reducing the increase in the current density (I), and thus the general corrosion rate, as the corrosion potential ($E_{corr}$) increases across the surface of the steel alloy. Eventually, the corrosion potential ($E_{corr}$) reaches the pitting breakdown potential ($E_b$), at which point the current density (I) increases dramatically, resulting in pitting corrosion, crevice corrosion, and/or other forms of localized corrosion on the surface of the steel alloy component. The localized corrosion may continue to occur until the corrosion potential ($E_{corr}$) decreases below the repassivation potential ($E_{rp}$).

Polarization scans are often performed in laboratories having the capability to accurately and precisely measure voltages and currents. For example, a sample of a steel alloy component may be connected to a variable power supply and a sensor and immersed in an electrolyte. As the voltage across the sample is varied, the current induced across the sample may be measured and graphed to produce a characteristic polarization curve for the particular steel alloy component being tested. The characteristic polarization curve for the particular steel alloy component may then be used to predict the rate and/or onset of various forms of corrosion for components containing the steel alloy.

The characteristic polarization curve, however, does not typically reflect any changes in corrosion rates attributable to pollution or contaminants deposited or precipitated onto the steel alloy component during operations. For example, ambient air flowing into a compressor often includes various amounts of moisture, salts, acids, and other pollution and contaminants that may deposit or precipitate onto various components inside the compressor. The build-up of pollution and contaminants on the components results in an environment conducive to increased levels of general, crevice, and/or pitting corrosion on the components that are not typically reflected in the characteristic polarization curve.

To adjust the characteristic polarization curve for actual conditions experienced during operations, several samples must be taken after operation, analyzed, and then recreated as best as possible in a laboratory for testing to determine what effect, if any, the pollution or contaminants have on the polarization curve. The testing generally requires some amount of disassembly and reassembly to obtain a suitable sample of the component, during which time the component may not be available for operation. As a result, a system and method for performing a polarization scan in situ would be useful in reducing the disassembly and reassembly associated with obtaining a suitable sample.

BRIEF DESCRIPTION OF THE INVENTION

Aspects and advantages of the invention are set forth below in the following description, or may be obvious from the description, or may be learned through practice of the invention.

One embodiment of the present invention is a system for performing an in-situ polarization scan of a component surface. The system includes a sensor connected to the component surface at a sensor connection, and the sensor generates a signal reflective of a current flow at the sensor connection. A power supply connected to the component surface at an electrical connection produces a voltage potential at the electrical connection. An electrolyte coats the sensor connection and the electrical connection on the component surface.

Another embodiment of the present invention is a method for performing an in-situ polarization scan of a component surface. The method includes sensing a current flow on the component surface, generating a signal reflective of the current flow on the component surface, and generating a voltage potential at an electrical connection on the component surface. The method further includes placing an electrolyte over at least a portion of the component surface and the electrical connection.

In another embodiment, a method for performing an in-situ polarization scan of a component surface includes sensing a current flow on the component surface, generating a voltage potential on the component surface, and placing an electrolyte over at least a portion of the component surface.

Those of ordinary skill in the art will better appreciate the features and aspects of such embodiments, and others, upon review of the specification.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Figure 1:
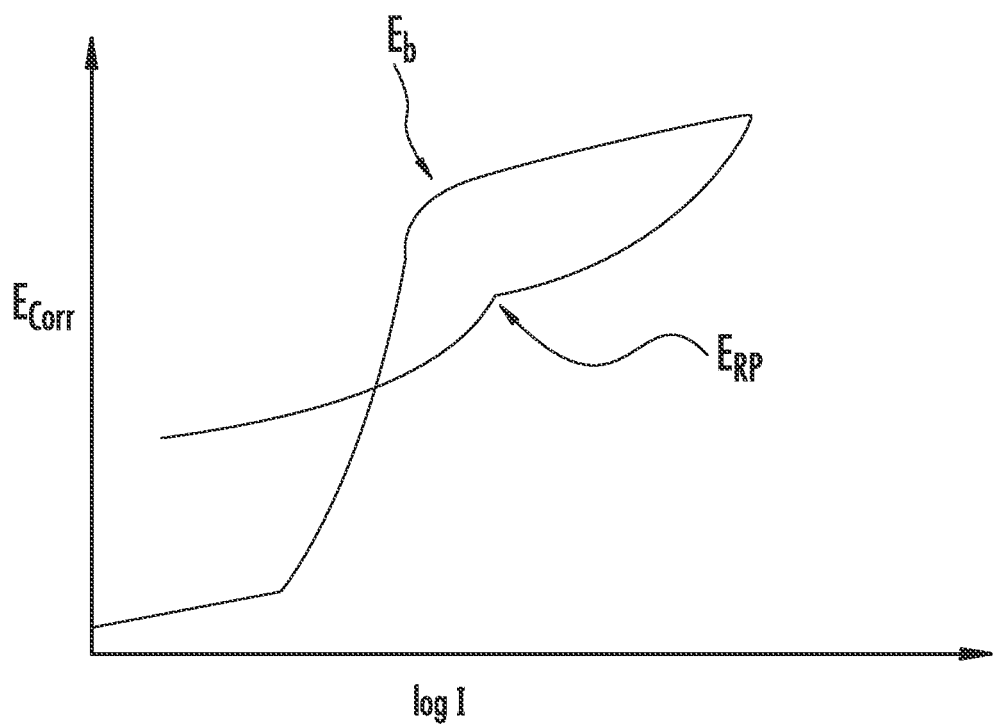
FIG. 1 is an exemplary polarization graph.

Reference will now be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention.

Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

Embodiments within the scope of the present invention provide a system and method for performing an in situ electrochemical polarization scan on a component. The in situ polarization scan may thus reflect the actual corrosive environment existing on the component without requiring substantial disassembly and reassembly of the component. The resulting graph of corrosion potential versus current density may be compared to historical polarization scans to schedule future maintenance and repair actions based on the predicted future corrosion rates of the component.

Figure 2:
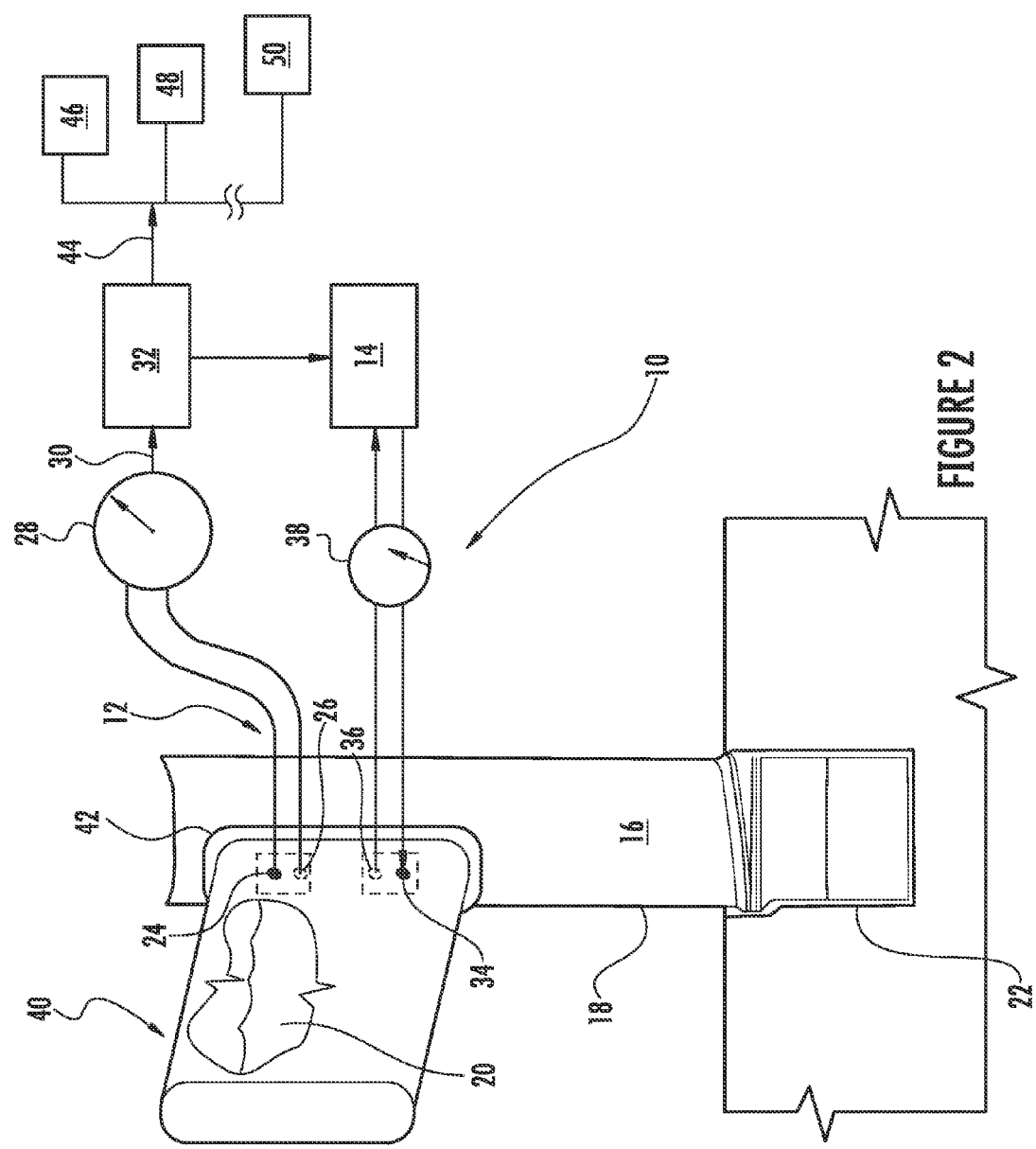
FIG. 2 is a simplified diagram of a system according to an embodiment of the present invention.

FIG. 2 provides a simplified diagram of a system 10 according to one embodiment of the present invention. In this particular embodiment, the system 10 generally includes a sensor 12 and a power supply 14 connected to a surface 16 of a component 18 being scanned. The system 10 further includes an electrolyte 20 that coats or covers at least a portion of the surface 16 of the component 18 being scanned. The component 18 may comprise any part of machinery or equipment on which a polarization scan is to be conducted. For example, the component 18 illustrated in FIG. 2 is a blade that might be included in a compressor, although embodiments of the present invention are not limited to any particular component unless specifically recited in the claims. As shown in FIG. 2, a nonconductive liner 22 may be installed around the component 18 to electrically insulate the component 18 from any stray currents that may affect the accuracy or sensitivity of the sensor 12.

The sensor 12 generally connects to the component surface 16 at a sensor connection 24 and also to a reference electrode 26 in the electrolyte 20 to complete the electrical circuit. The sensor 12 may comprise any instrument capable of detecting and/or measuring a current flow, current density, and/or voltage potential across the sensor connection 24 and the reference electrode 26. For example, the sensor 12 may comprise a voltmeter 28 or an ammeter capable of measuring or controlling the voltage potential across the sensor connection 24 and the reference electrode 26. The sensor 12 may produce a signal 30 reflective of the current flow, current density, and/or voltage potential across the sensor connection 24 and the reference electrode 26. The signal 30 may comprise, for example, a current or voltage magnitude which may be proportional to the amount and/or rate of general corrosion occurring on the component surface 16. The signal 30 may be manually interpreted and acted on by an operator to adjust the power supply 14 as desired. Alternately, or in addition, as shown in FIG. 2, the system 10 may include a controller 32 configured or programmed to receive the signal 30 and adjust the power supply 14. As described herein, the technical effect of the controller 32 is to adjust the power supply 14 to achieve a desired voltage and/or current out of the power supply 14. The controller 32 may be a stand alone component, such as a potentiometer, or a sub-component included in any computer system known in the art, such as a laptop, a personal computer, a mini computer, or a mainframe computer. The various controller and computer systems discussed herein are not limited to any particular hardware architecture or configuration. Embodiments of the systems and methods set forth herein may be implemented by one or more general-purpose or customized controllers adapted in any suitable manner to provide the desired functionality. For example, the controller 32 may be adapted to provide additional functionality, either complementary or unrelated to the present subject matter. When software is used, any suitable programming, scripting, or other type of language or combinations of languages may be used to implement the teachings contained herein. However, some systems and methods set forth and disclosed herein may also be implemented by hard-wired logic or other circuitry, including, but not limited to, application-specific circuits. Of course, various combinations of computer-executed software and hard-wired logic or other circuitry may be suitable as well.

The power supply 14 may comprise any variable source of direct current and may connect to the component surface 16 at an electrical connection 34 and also to a counter electrode 36 in the electrolyte 20 to complete the electrical circuit. For example, the power supply 14 may comprise a battery capable of providing 5 to 500 milliamps of current at voltages less than 15 V DC. However, the size and capacity of the power supply 14 will depend on the particular use, and the present invention is not limited to any particular size or capacity of the power supply 14 unless specifically recited in the claims. As shown in FIG. 2, an ammeter 38 may be used with the power supply 14 to measure and/or supply the desired current and voltage to the component surface 16.

As shown in FIG. 2, the electrolyte 20 coats or covers the sensor connection 24, reference electrode 26, electrical connection 34, and counter electrode 36. The electrolyte 20 may comprise any fluid capable of conducting electron flow. For example, the electrolyte 20 may comprise a solution of bicarbonate of soda, salt water, or other ionized solutions known to one of ordinary skill in the art. The electrolyte 20 may be held in place by a container 40. A seal 42 between the container 40 and the component surface 16 may hold the container 40 in place so that the electrolyte 20 covers the sensor connection 24, reference electrode 26, electrical connection 34, and counter electrode 36. The seal 42 may comprise any suitable device for connecting one component to another. For example, the seal 42 may comprise magnets, suction cups, adhesives, or other suitable structures known to one of ordinary skill in the art for providing a sealing engagement between the container 40 and the component surface 16.

During operation of the system 10, the sensor 12 and the power supply 14 are connected to the component surface 16 at the sensor connection 24 and electrical connection 34 respectively. The container 40 containing the electrolyte 20 is placed over the sensor connection 24 and the electrical connection 34 and may be held in place by the seal 42, if present. In this manner, the electrolyte 20 mixes with any deposits or contaminants on the component surface 16 and provides the conductive medium that enables electron flow between the sensor connection 24 and the reference electrode 26 and between the electrical connection 34 and the counter electrode 36.

Once an equilibrium is reached between the electrolyte 20 and any deposits or contaminants on the component surface 16, the sensor 12 may be used to sense the current flow, current density, and/or voltage potential between the sensor connection 24 and the reference electrode 26 and generate the signal 30 reflective of the current flow, current density, or voltage potential between the sensor connection 24 and the reference electrode 26. The power supply 14 may then be adjusted, either manually or through the use of the controller 32, to produce or generate a voltage potential or current flow between the electrical connection 34 and the counter electrode 36. The sensor 12 may again be used to sense any change in the current flow, current density, and/or voltage potential between the sensor connection 24 and the reference electrode 26, and the process is repeated as desired to determine the current flow, current density, and/or voltage potential between the sensor connection 24 and the reference electrode 26 associated with each voltage potential or current flow provided between the electrical connection 34 and the counter electrode 36.

The collection of sensor 12 measurements and associated voltage potentials may be graphed to produce a component-specific polarization graph or curve for the component 18 that reflects the actual corrosive environment for the component 18. If desired, the controller 32 may be programmed or configured to compare the component-specific polarization graph to a predetermined limit, such as, for example, the characteristic polarization graph previously described. Alternately, or in addition, the controller 32 may be programmed or configured to generate an output signal 44 that reflects repair 46 and/or maintenance 48 schedules, a useful life projection 50 for the component 18, or another scheduling parameter based on the component-specific polarization graph. In this manner, the operation, maintenance, and/or repair schedule for the component 18 may be adjusted to reflect the actual corrosive conditions present on the component 18.

It is anticipated that embodiments of the present invention as shown in FIG. 2 will be portable devices that can readily attach to a metallic surface in its local environment without requiring much, if any, component disassembly and subsequent re-assembly. As a result, embodiments of the present invention may substantially reduce the amount of time needed to set up and complete a polarization scan. In addition, the information obtained from the polarization scan will more accurately reflect the actual corrosive conditions present on the component which will allow more repair and/or maintenance schedules to more accurately reflect the actual amount of corrosion occurring on the component.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other and examples are intended to be within the scope of the claims if they include structural elements that do not differ from the literal language of the claims, or if they include equivalent structural elements with insubstantial differences from the literal languages of the claims.

What is claimed is:

1. A system for performing an in-situ polarization scan of a component surface comprising:
    a. a sensor physically connected to the component surface at a sensor connection located on the component surface, wherein said sensor generates a signal reflective of a current flow at said sensor connection on the component surface;
    b. a power supply physically connected to the component surface at an electrical connection located on the component surface, wherein said power supply produces a voltage potential at said electrical connection on the component surface; and
    c. an electrolyte coating said sensor connection and said electrical connection on the component surface.

2. The system as in claim 1, further comprising a container covering said sensor connection and said electrical connection.

3. The system as in claim 2, wherein said container holds said electrolyte in contact with said sensor connection and said electrical connection.

4. The system as in claim 2, further comprising a seal between said container and the component surface.

5. The system as in claim 1, further comprising a controller that receives said signal reflective of said current flow at said sensor connection.

6. The system as in claim 5, wherein said controller adjusts said voltage potential at said electrical connection.

7. The system as in claim 5, wherein said controller compares at least one of said current flow or said voltage potential to a predetermined limit.

8. The system as in claim 5, wherein said controller generates an output signal, wherein said output signal includes at least one of repair or maintenance scheduling information.

9. A method for performing an in-situ polarization scan of a component surface comprising:
    a. sensing a current flow on the component surface;
    b. generating a signal reflective of said current flow on the component surface;
    c. physically connecting a power supply to an electrical connection located on the component surface;
    d. generating a voltage potential at said electrical connection on the component surface with said power supply; and
    e. placing an electrolyte over at least a portion of the component surface and said electrical connection.

10. The method as in claim 9, further comprising adjusting said voltage potential at said electrical connection on the component surface based on said signal reflective of said current flow on the component surface.

11. The method as in claim 9, further comprising placing a container containing said electrolyte over at least a portion of the component surface and said electrical connection.

12. The method as in claim 11, further comprising sealing said container to the component surface.

13. The method as in claim 9, further comprising comparing at least one of said current flow or said voltage potential to a predetermined limit.

14. The method as in claim 9, further comprising generating an output signal, wherein said output signal includes at least one of repair or maintenance scheduling information.

15. A method for performing an in-situ polarization scan of a component surface comprising:
    a. physically connecting a sensor to the component surface at a sensor connection located on the component surface;
    b. sensing a current flow at said sensor connection on the component surface;
    c. physically connecting a power supply to an electrical connection located on the component surface;
    d. generating a voltage potential at said electrical connection on the component surface; and
    e. placing an electrolyte over at least a portion of the component surface.

16. The method as in claim 15, further comprising adjusting said voltage potential on the component surface based on said current flow on the component surface.

17. The method as in claim 15, further comprising placing a container containing said electrolyte over at least a portion of the component surface.

18. The method as in claim 15, further comprising comparing at least one of said current flow or said voltage potential to a predetermined limit.

19. The method as in claim 15, further comprising generating an output signal, wherein said output signal includes at least one of repair or maintenance scheduling information.

* * * * *